US012728207B2

(12) United States Patent
Dasbach et al.

(10) Patent No.: US 12,728,207 B2
(45) Date of Patent: Sep. 8, 2026

(54) INJECTOR DEVICE WITH DISTRACTION MECHANISM

(71) Applicant: Sanofi, Paris (FR)

(72) Inventors: Uwe Dasbach, Frankfurt am Main (DE); Kai Scheinert, Frankfurt am Main (DE); Daniel Auernhammer, Frankfurt am Main (DE); Florian Schauderna, Frankfurt am Main (DE); Thomas Mark Kemp, Herts (GB); Tim Schuller, Herts (GB); Robbie Wilson, Herts (GB); Michael Noble, Herts (GB); Ryan Anthony McGinley, Herts (GB)

(73) Assignee: Sanofi, Paris (FR)

( * ) Notice: Subject to any disclaimer, the term of this patent is extended or adjusted under 35 U.S.C. 154(b) by 1011 days.

(21) Appl. No.: 17/915,757

(22) PCT Filed: Apr. 1, 2021

(86) PCT No.: PCT/EP2021/058750
§ 371 (c)(1),
(2) Date: Sep. 29, 2022

(87) PCT Pub. No.: WO2021/198483
PCT Pub. Date: Oct. 7, 2021

(65) Prior Publication Data

US 2023/0218824 A1 Jul. 13, 2023

(30) Foreign Application Priority Data

Apr. 3, 2020 (EP) .................................... 20315115

(51) Int. Cl.
*A61M 5/20* (2006.01)
*A61M 5/32* (2006.01)

(52) U.S. Cl.
CPC ............ *A61M 5/2033* (2013.01); *A61M 5/32* (2013.01)

(58) Field of Classification Search
CPC .............................. A61M 5/2033; A61M 5/32
See application file for complete search history.

(56) References Cited

U.S. PATENT DOCUMENTS

2012/0046614 A1 2/2012 Andreoni
2017/0326298 A1 11/2017 Hourmand et al.
(Continued)

FOREIGN PATENT DOCUMENTS

CA 2610129 A1 5/2009
CN 204233541 U 4/2015
(Continued)

OTHER PUBLICATIONS

International Preliminary Report on Patentability in International Appln. No. PCT/EP2021/058750, mailed on Oct. 13, 2022, 9 pages.
(Continued)

*Primary Examiner* — Dung T Ulsh
(74) *Attorney, Agent, or Firm* — Fish & Richardson P.C.

(57) ABSTRACT

This disclosure relates to features of an injection device arranged to provide a sensory distraction to a user during insertion of a needle into flesh. According to a first aspect, an injector device includes a housing having a proximal end and a distal end, and configured to receive a container of medicament, a needle housing for holding a needle in a position at the distal end of the housing, and a needle sleeve mounted within the housing, wherein the needle sleeve and needle housing are moveable relative to one another by a user action between a first configuration in which the needle sleeve would enclose a needle, and a second configuration in which a needle would extend from the needle sleeve in the distal direction, wherein the needle sleeve comprises a
(Continued)

portion configured to vibrate and/or rotate during motion between the first configuration and the second configuration.

18 Claims, 6 Drawing Sheets

(56) References Cited

U.S. PATENT DOCUMENTS

| | | | | |
|---|---|---|---|---|
| 2018/0353704 | A1* | 12/2018 | Helmer .............. | A61M 5/2466 |
| 2019/0001070 | A1* | 1/2019 | Wendland .......... | A61M 5/3202 |
| 2019/0125983 | A1 | 5/2019 | Staton et al. | |

FOREIGN PATENT DOCUMENTS

| | | | | |
|---|---|---|---|---|
| DE | 102011015073 | A1 | 9/2012 | |
| EP | 2468330 | | 6/2012 | |
| EP | 2468330 | A1 * | 6/2012 | .......... A61M 5/2033 |
| EP | 2540329 | | 1/2013 | |
| JP | 2002-065648 | A | 3/2002 | |
| JP | 2012-071112 | A | 4/2012 | |
| JP | 2013-509930 | A | 3/2013 | |
| WO | WO 2003/024513 | | 3/2003 | |
| WO | WO 2011/012903 | | 2/2011 | |
| WO | WO 2011/055150 | A2 | 5/2011 | |

OTHER PUBLICATIONS

International Search Report and Written Opinion in International Appln. No. PCT/EP2021/058750, mailed on Aug. 16, 2021, 14 pages.

* cited by examiner

INJECTOR DEVICE WITH DISTRACTION MECHANISM

CROSS REFERENCE TO RELATED APPLICATIONS

The present application is the national stage entry of International Patent Application No. PCT/EP2021/058750, filed on Apr. 1, 2021, and claims priority to Application No. EP 20315115.4, filed on Apr. 3, 2020, the disclosures of which are incorporated herein by reference.

TECHNICAL FIELD

This disclosure relates to features of an injection device arrange to provide a sensory distraction to a user during insertion of a needle into flesh.

BACKGROUND

Injection devices, such as auto-injectors, are known in the art for dispensing a medicament to the injection site of a patient. Such injection devices often comprise a body and a cap, a needle syringe located in the body and the cap removably attached to the body to shield the needle of the needle syringe. To dispense the medicament, the cap is first removed from the body to expose the needle. The needle is then inserted into the body of the patient at the injection site to dispense the medicament.

The insertion of the needle into the body of a user is often associated with pain and discomfort for the user. Additionally, the user may become anxious and tense during needle insertion, resulting in additional pain.

SUMMARY

According to a first aspect, this specification discloses an injector device comprising: an elongate housing having a proximal end and a distal end, and configured to receive a container of medicament; a needle housing for holding a needle in a position at the distal end of the elongate housing; and a needle sleeve mounted within the housing, wherein the needle sleeve and needle housing are moveable relative to one another by a user action between a first configuration in which the needle sleeve would enclose a needle held in the needle holder, and a second configuration in which a needle held in the needle housing would extend from the needle sleeve in the distal direction, wherein the needle sleeve comprises a portion configured to vibrate and/or rotate using energy from the user action during motion between the first configuration and the second configuration.

In the first configuration the needle sleeve may be in an extended position in which the needle sleeve at least partially extends from the distal end of the housing. In the second configuration the needle sleeve may be in a retracted position in which the needle sleeve is received further within the housing than in the extended position. The needle housing may be substantially fixed relative to the elongate housing such that the needle is shrouded when the needle sleeve is in the extended position and the needle is exposed when the needle sleeve is in the retracted position.

The needle sleeve may comprise an outer sleeve and an inner sleeve, the inner sleeve comprising the portion configured to vibrate and/or rotate. The outer sleeve may extend beyond the inner sleeve in the distal direction.

The inner sleeve may comprise one or more recessed tracks. The housing may comprise one or more engaging portions arranged to couple with the one or more tracks to cause vibration and/or rotation of the inner sleeve during motion of the needle sleeve between the extended position and the retracted position. The one or more tracks may extend in a spiral around the inner sleeve and wherein the inner sleeve is free to rotate relative to the elongate housing. The one or more tracks may be in the form of a zig-zag on the surface of the inner sleeve, thereby causing the inner sleeve to vibrate during motion between the first configuration and the second configuration. The one or more engaging portions may comprise a ratchet arrangement configured to resist movement between the first and second configurations and to not resist movement between the second and first configurations.

The user action may comprise manually depressing the elongate housing laterally in the distal direction.

The portion of the needle sleeve configured to vibrate and/or rotate may comprise one or more brushes extending in the distal direction. The portion of the needle sleeve configured to vibrate and/or rotate may alternatively or additionally comprise one or more protrusions and/or ridges extending in the distal direction. The portion of the needle sleeve configured to vibrate and/or rotate may alternatively or additionally comprise one or more piezoelectric devices.

The injection device may further comprise: a piston rod moveable longitudinally within the housing; and a piston spring configured to bias the piston rod towards a distal end of the housing to engage a container of medicament when received within the housing, wherein the needle sleeve is configured to supress vibration and/or rotation of the portion during longitudinal motion of the piston rod in the distal direction.

The injection device may further comprise: a piston rod moveable longitudinally within the housing; and a piston spring configured to bias the piston rod towards a distal end of the housing to engage a container of medicament when received within the housing, wherein the portion of the needle sleeve configured to vibrate and/or rotate is further configured to vibrate and/or rotate during longitudinal motion of the piston rod in the distal direction.

The needle sleeve may be fixed relative to the elongate housing. In the first configuration, the needle housing may be in a retracted position in which the needle held in the needle housing is shrouded by the needle sleeve. In the second configuration the needle housing may be in an extended position in which the needle in the needle housing extends beyond the needle sleeve in the distal direction.

The injection device may further comprise a needle for expelling medicament from the injection device, the needle held in a position at the distal end of the elongate housing that is substantially fixed relative to the elongate housing such that the needle is shrouded when the needle sleeve is in the extended position and the needle is exposed when the needle sleeve is in the retracted position.

The injection may further comprise a container of medicament received within the housing.

According to a further aspect, this specification discloses a method of using the injection device, the method comprising: preparing the injection device in the first configuration; and applying a user action to change the configuration of the user device from the first configuration to the second configuration.

According to a further aspect, this specification discloses a method for causing vibration and/or rotation of a portion of a portion of an injection device, the injection device having a distal end and a proximate end, the distal end comprising a needle sleeve and a needle, the method comprising: moving, under a user action, the injection between a first configuration, in which a needle sleeve encloses the needle, and a second configuration, in which the needle extends beyond the needle sleeve in the distal direction; and vibrating and/or vibrating a portion of a distal end of the injection device during motion between the first configuration and the second configuration using energy from the user action.

BRIEF DESCRIPTION OF THE FIGURES

Embodiments will now be described by way of non-limiting examples with reference to the accompanying drawings, in which.

DETAILED DESCRIPTION

Figure 1A:
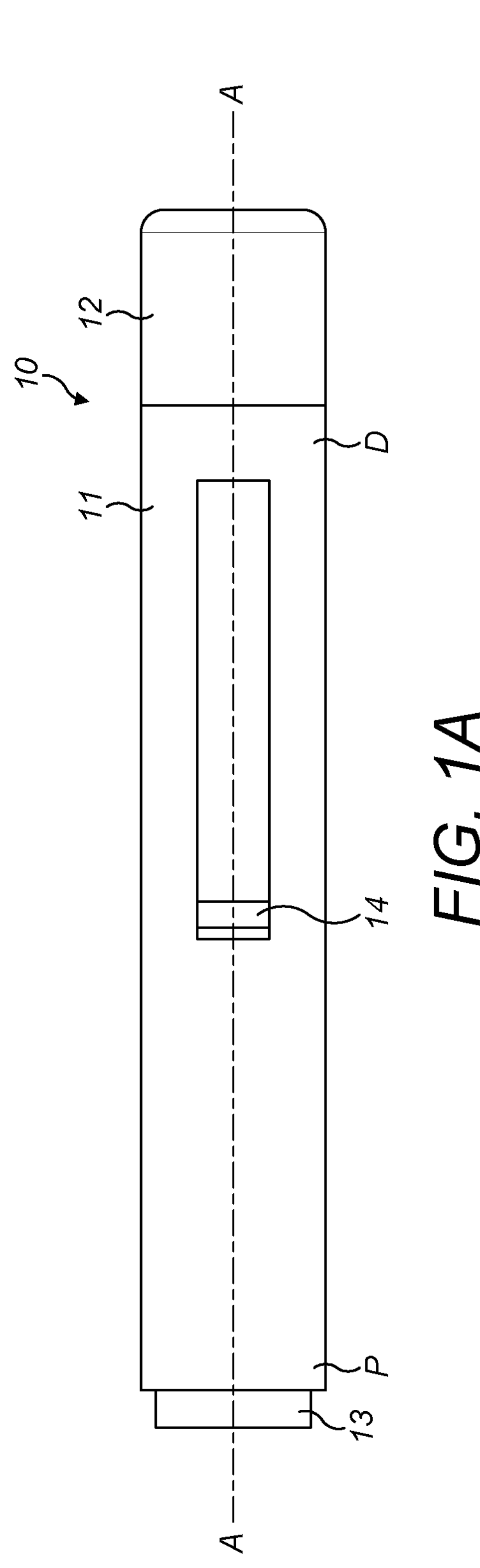
FIGS. 1*a* and 1*b* show an exemplary drug delivery device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 3 ml. Another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 50 ml). Yet another device may comprise a pre-filled syringe within a housing of the device. The syringe may be fixed within the housing or may be moveable within the housing, for example from a retracted position to an operation extended position.

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
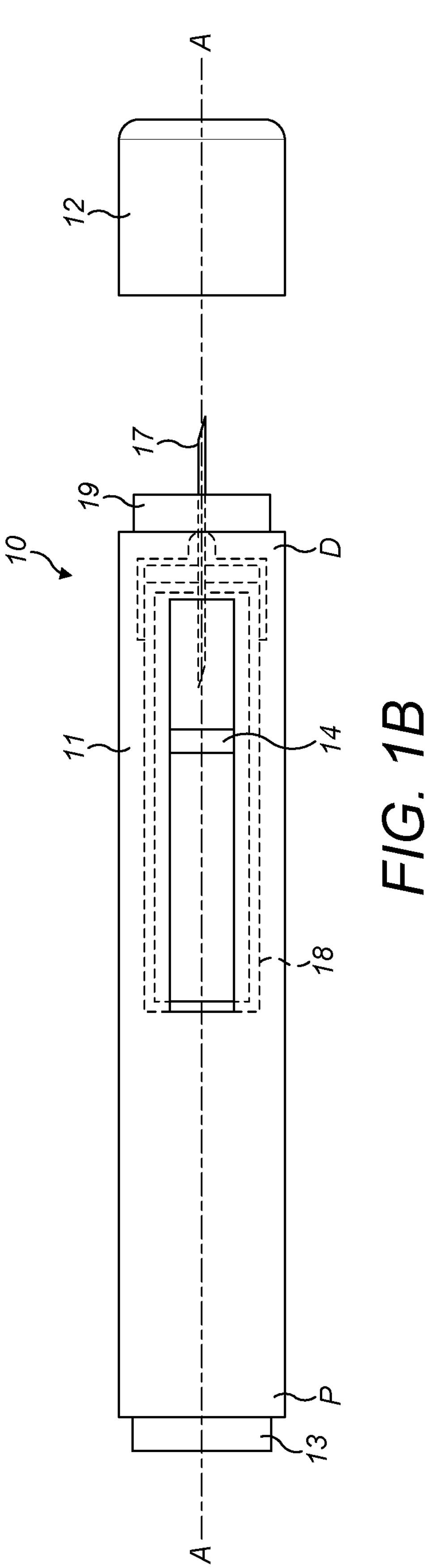

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge or pre-filled syringe that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11. In some embodiments, the needle sleeve 19 can alternatively be fixed relative to the housing 11, or be formed as part of the housing 11.

Insertion of needle 17 can occur via several mechanisms. For example, needle 17 may be fixedly located relative to housing 11, for example in a needle housing (not shown), and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A and 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14 (also referred to as a "plunger"). Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17. Such distal movement may be referred to as "depression" of the piston 14.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the cartridge 18 within housing 11 is moved in a proximal direction relative to housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between needle 17 and housing 11 can be locked with a locking mechanism. In addition, button 13 or other components of device 10 can be locked as required.

In some embodiments, the injection device may be a needless device, such as a jet injector. In devices of this type, a needle is not present. Medicament is administered by expelling the medicament from the injection device as a high pressure stream of liquid that penetrates the skin of the recipient.

Figure 2:
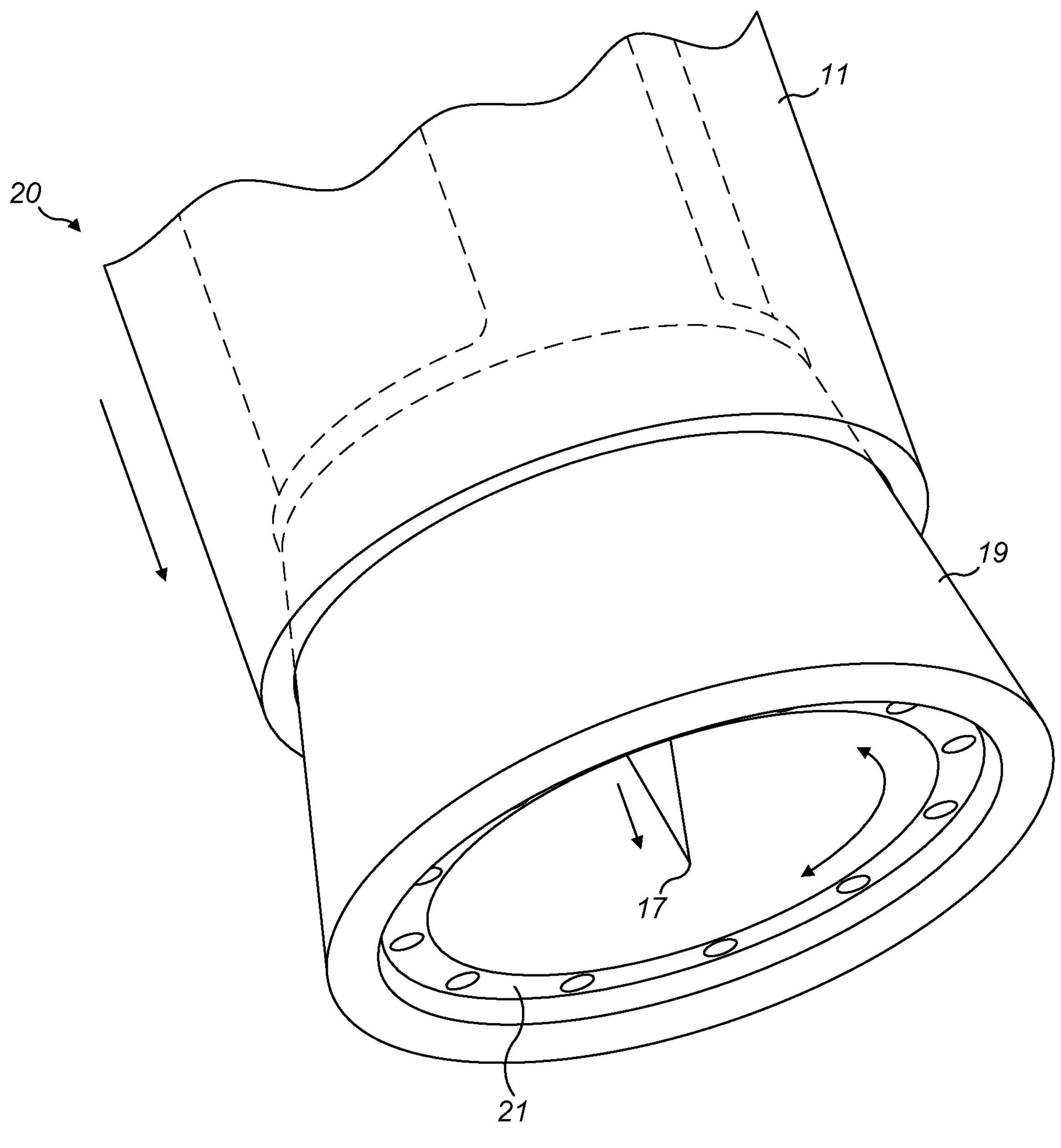
FIG. 2 shows a view of an example of the distal end of the injection device.

FIG. 2 shows a view of an example of the distal end of the injection device. The distal end 20 of the injection device comprises a needle sleeve 19 that comprises a portion 21 (also referred to herein as the "distraction portion") configured to vibrate and/or rotate during motion of the needle sleeve 19 between the extended position and the retracted position. The needle sleeve 19 is arranged to shroud (i.e., cover) the needle 17 when in the extended position and expose the needle 17 in the retracted position. The configuration where the needle sleeve 19 shrouds a needle may be referred to herein as a "first configuration" and the configuration in which the needle is exposed may be referred to as a "second configuration". In FIG. 2, the needle sleeve 19 is in the extended position (i.e. the first configuration).

A user actuation/action causes the needle sleeve 19 to move between the extended position and the retracted position. The needle sleeve 19 is configured to use energy from the user actuation/action to cause vibration and/or rotation of the distraction portion 21, thereby providing a sensory distraction from the ingress of the needle 17 into the flesh.

For example, when performing an injection a user may place the distal end of the needle sleeve 19 when in the extended position on a target injection site on skin. The user applies a force to the housing 11 in the distal direction, for example by gripping and pushing it towards the injection site, causing the housing 11 to move in the lateral direction towards the injection site. This action is referred to herein as "depression" of the housing. The needle sleeve 19 retracts into the housing 11 as the housing 11 moves in the lateral direction. As the needle 17 is fixed relative to the housing, the needle 17 extends from the needle sleeve 19 and pierces the skin at the injection site during this motion of the housing.

During retraction of the needle sleeve 19 into the housing, the distraction portion 21 provides sensory stimulation in the region of the injection site by vibrating and/or rotating. The energy required for providing such vibration/rotation is extracted from the depression of the housing 11. For example, ridges within the needle sleeve 19/distraction portion 21 may rub/vibrate against inner surfaces of the housing 11 to create a vibrating sensation during depression to mask pain of needle 17 insertion. Other examples of how the vibration/rotation of the distraction portion 21 can be provided will be described below.

In some embodiments, such as the one shown in FIG. 2, the distraction portion 21 is provided by one or more rings at the distal end of the needle sleeve 19 that are configured to rotate and/or oscillate during depression of the housing 11. The one or more rings/distraction portion 21 may be located such that they are not under pressure during depression of the housing 11, i.e., that they do not directly contact the sin at the injection site, even under high pressure.

In addition to vibrating/rotating during the retraction of the needle housing 19, the distraction portion 21 may, in some embodiments, also vibrate and/or rotate during the injection itself—i.e., during depression of a plunger/bung/piston into the medicament cartridge. The plunger/piston may engage with the needle sleeve 19 to use energy from the plunger depression to cause the vibration/rotation of the needle sleeve 19. The needle sleeve 19 may be provided with internal features that engage with the plunger/piston to provide the vibration/rotation. For example, the inside of the needle sleeve 19 may be rough and in contact with the piston/plunger, so that motion of the piston/plunger causes vibration of the needle sleeve 19. Alternatively, the needle sleeve may have internal tracks that engage with features on the piston/plunger in an analogous way to features on the housing 11. This can provide a distraction to the user throughout the full course of the injection—i.e., from needle insertion to the end of the medicament delivery.

In other embodiments, the needle sleeve 19 is configured not to rotate/vibrate during depression of the piston into the medicament cartridge. This can prevent the needle 17 being moved during the expulsion of medicament, which may cause additional pain.

In some embodiments, the needle sleeve 19 may be fixed relative to the housing 11, with the needle housing moveable relative to the housing 11 between a position in which the needle 17 held in the needle housing is shrouded by the needle sleeve 19 (i.e., the first configuration) and a position in which the needle 17 held in the needle housing extends beyond the needle sleeve 19 in the distal direction (i.e., the second configuration). The portion of the needle sleeve 19 configured to vibrate and/or rotate uses energy from the user action during motion between the first configuration and the second configuration.

In general, relative motion between the needle sleeve 19 and the needle housing can be used to move between a first configuration, in which a needle 17 held by the needle housing is shrouded by the needle sleeve, and a second configuration, in which a needle 17 held by the needle housing extends beyond the needle sleeve 19 in the distal direction. Energy from this relative motion is used to vibrate and/or rotate a portion of the needle sleeve 19 in order to provide a distraction. One of the needle sleeve 19 and needle housing may be fixed relative to the housing 11. Alternatively, both the needle sleeve 19 and needle housing may be moveable with respect to the housing 11.

In needle free injection devices, a vibrating and/or rotating portion may be present at the distal end of the housing (i.e., the part of the injection device that contacts the skin of the patient during the needless injection) to provide a distraction during skin penetration by the high pressure medicament stream. A mechanism used to generate the high pressure stream of medicament may also be used to provide the energy for the vibration and/or rotation of the vibrating and/or rotating portion. Alternatively, the vibrating and/or rotating portion may be powered separately.

Figure 3:
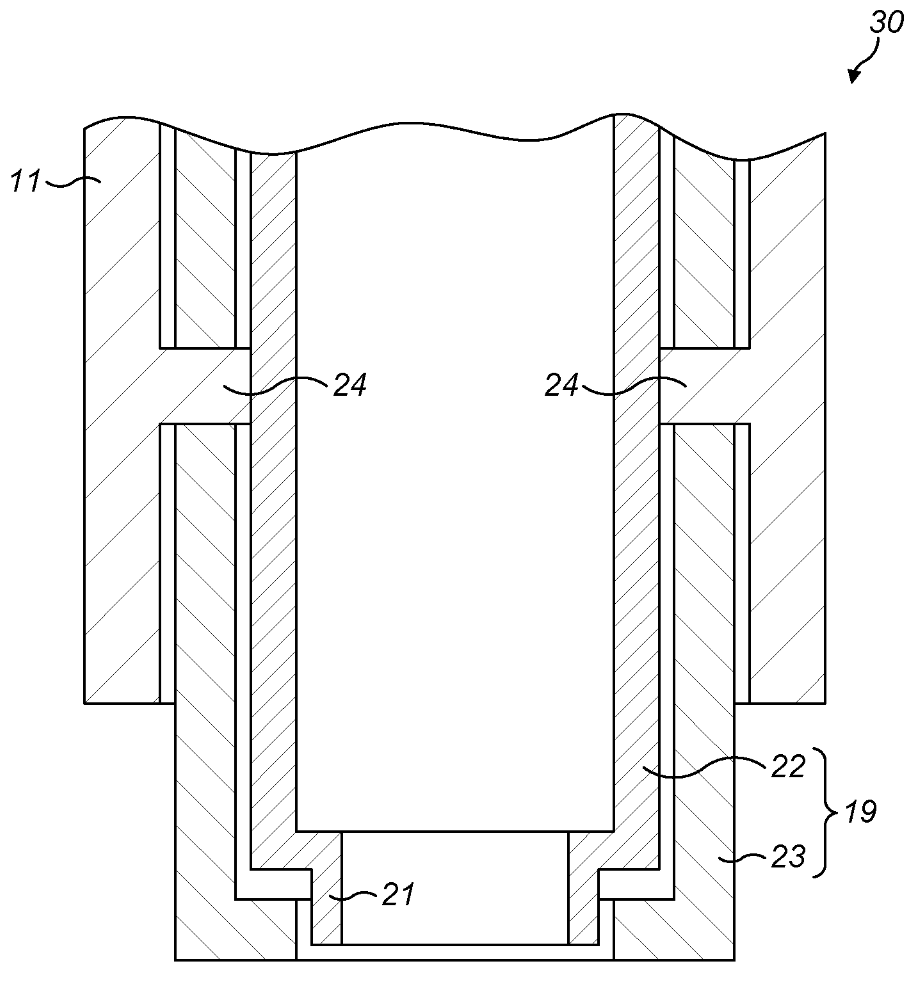
FIG. 3 shows a cross sectional view of an embodiment of an injection device.

FIG. 3 shows a cross sectional view of an embodiment of an injection device 30. In some embodiments, such as the embodiment shown here, the needle sleeve 19 comprises an inner sleeve 22 and an outer sleeve 23. The inner sleeve 22 comprises the distraction portion 21—i.e., the portion configured to vibrate and/or rotate during depression of the housing 11. The outer sleeve 23 may extend further in the distal direction than the inner sleeve 22 such that the outer sleeve 23 will contact skin of the user when in use and prevent the inner sleeve 22 directly contacting the skin of the user/only exerting a light pressure on the skin of the user. In this way, motion of the inner sleeve will not grip the skin of the user and move it relative to the needle 17 during needle insertion, which could cause additional pain.

The inner sleeve 22 may be fully or partially (i.e., within some limits) free to rotate relative to the outer sleeve 23. The inner sleeve 22 may be vertically constrained relative to the outer sleeve 23. Such freedom and/or constraints may act limit any additional force required to depress the housing 11 during use.

The housing 11 comprises one or more engaging features 24 (also referred to herein as a "forcing features") arranged to engage with features on the surface of the inner sleeve 22 in order to transfer energy from motion of the housing 11 to the inner sleeve 22 in order to cause the distraction portion 21 to rotate and/or vibrate. For example, the surface of the inner sleeve 22 may be rough and/or comprise a plurality of bumps and/or ridges. As the one or more engaging features 24 pass over these features, friction between the one or more engaging features 24 and the surface features of the inner sleeve 22 causes the inner sleeve 22 to vibrate, thereby vibrating the distraction portion 21 of the needle sleeve 19.

Alternatively or additionally, the one or more engaging features 24 may engage with one or more tracks on the surface of the needle housing 19. The tracks may be on the inner sleeve 22 in embodiments where the needle sleeve 19 comprises an inner sleeve 22 and an outer sleeve 23. The tracks act to guide motion of the inner sleeve 22 relative to the housing 11 during depression of the housing. Embodiments in which engaging portions coupled to tracks on the inner sleeve 22 are described in further detail below with reference to FIGS. 5-6. In embodiments where the needle sleeve 19 is a single piece, the tracks may be on the surface of the needle sleeve 19, and cause the whole needle sleeve 19 to rotate or vibrate during depression of the housing 11.

In embodiments were multiple engaging portions 24 are present, the engaging portions 24 may be arranged symmetrically around the inside of the housing 11. Such an arrangement may assist in maintaining the inner sleeve in a central position. For example, in the embodiment shown, the engaging portions 24 are arranged at radially opposing positions on the inside of the housing 11. However, the engaging portions 24 may be arranged in other symmetrical configurations, such as a configuration with three-fold rotational symmetry where the engaging portions 24 are arranged at 120-degree angular offsets around the inside of the housing 11, or a configuration with four-fold rotational symmetry where the engaging portions 24 are arranged at 90-degree angular offsets around the inside of the housing 11. Other regular angular offsets of the engaging portions 24 may alternatively be used.

In some embodiments, the engaging portions 24 have a symmetrical angular spacing around the inside of the housing 11 relative to the longitudinal axis of the housing, but are offset in the lateral/longitudinal direction. Such an arrangement gives the engaging portions 24 a discrete screw-like symmetry. For example, a second engaging portion may be arranged at a 120-degree angular offset to a first engaging portion, but offset in the lateral direction. A third engaging portion may be arranged at a 120-degree angular offset to a second engaging portion, but offset in the lateral direction. Thus, engaging portions 24 are symmetrically arranged in their angular coordinate, but displaced in the longitudinal direction. Such an arrangement may be beneficial to keep the needle housing 19 centred when the needle housing has a single track on its surface.

Figure 4A:
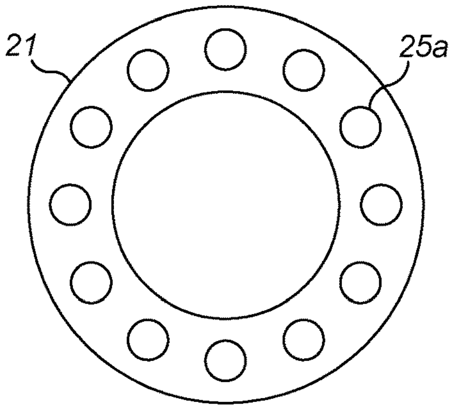
FIGS. 4*a-c* show examples of surface patterns at the distal end of the distraction portion of an injection device.
Figure 4B:
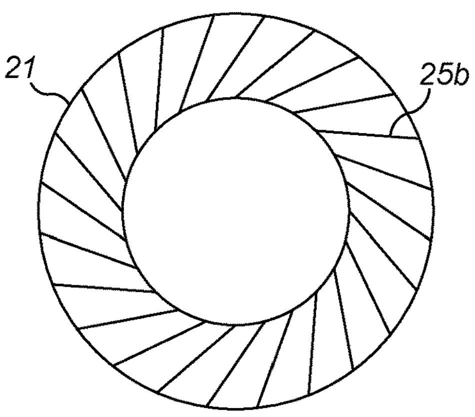
Figure 4C:
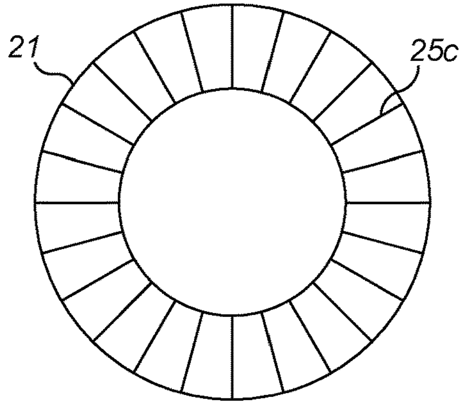

FIGS. 4*a*-*c* show examples of surface patterns at the distal end of the distraction portion of an injection device. In some embodiments, the distraction portion 21 of the needle sleeve 19 may comprise one or more surface features 25*a*-*c* arranged to provide sensory stimulation to a region around the injection site when the distraction portion vibrates and/or rotates. The protrusions 25*a*-*c* may contact the skin of the user during vibration/rotation of the distraction portion 21 in order to provide a distracting sensation to the user.

In some embodiments, the surface features 25*a*-*c* are arranged such that the outer sleeve 23 of the needle sleeve 19 only slightly extends beyond the surface features 25*a*-*c*. When in use, the surface features 25*a*-*c* will then only lightly contact the skin of the user in the region of the injection, thereby providing a distracting sensation without adversely affecting the depression of the housing 11 when in use or gripping and moving the skin of the user during needle 17 insertion. In other words, the surface features 25*a*-*c* only exert light pressure on the skin of the user during vibration and/or rotation of the distraction portion 21.

The surface features may comprise one or more protrusions from the surface of the distraction portion 21. The protrusions may, for example, comprise a plurality of bumps 25*a* on the surface of the distraction portion 21, as shown in FIG. 4*a*. The bumps 25*a* may be regularly or irregularly spaced on the surface of the distraction portion 21. The plurality of bumps 25*a* may have a regular or irregular shape. The protrusions may alternatively or additionally comprise ridges 25*b*, 25*c* on the surface of the distraction portion 21. The ridges 25*b* may be angled towards or away from the direction of rotation of the distraction potion, as shown in FIG. 4*b*. Alternatively, the ridges 25*c* may be aligned in a radial direction, as shown in FIG. 4*c*.

In some embodiments (not shown), the distraction portion 21 comprises one or more brushes extending in the distal direction. The brushes may extend slightly beyond the outer sleeve 23 of the needle sleeve 19 and flex when under pressure. During rotation and/or vibration of the distraction portion 21, the brushes provide a "tickling" sensation to distract the use from the pain of the needle 17 entering the skin.

Figure 5:
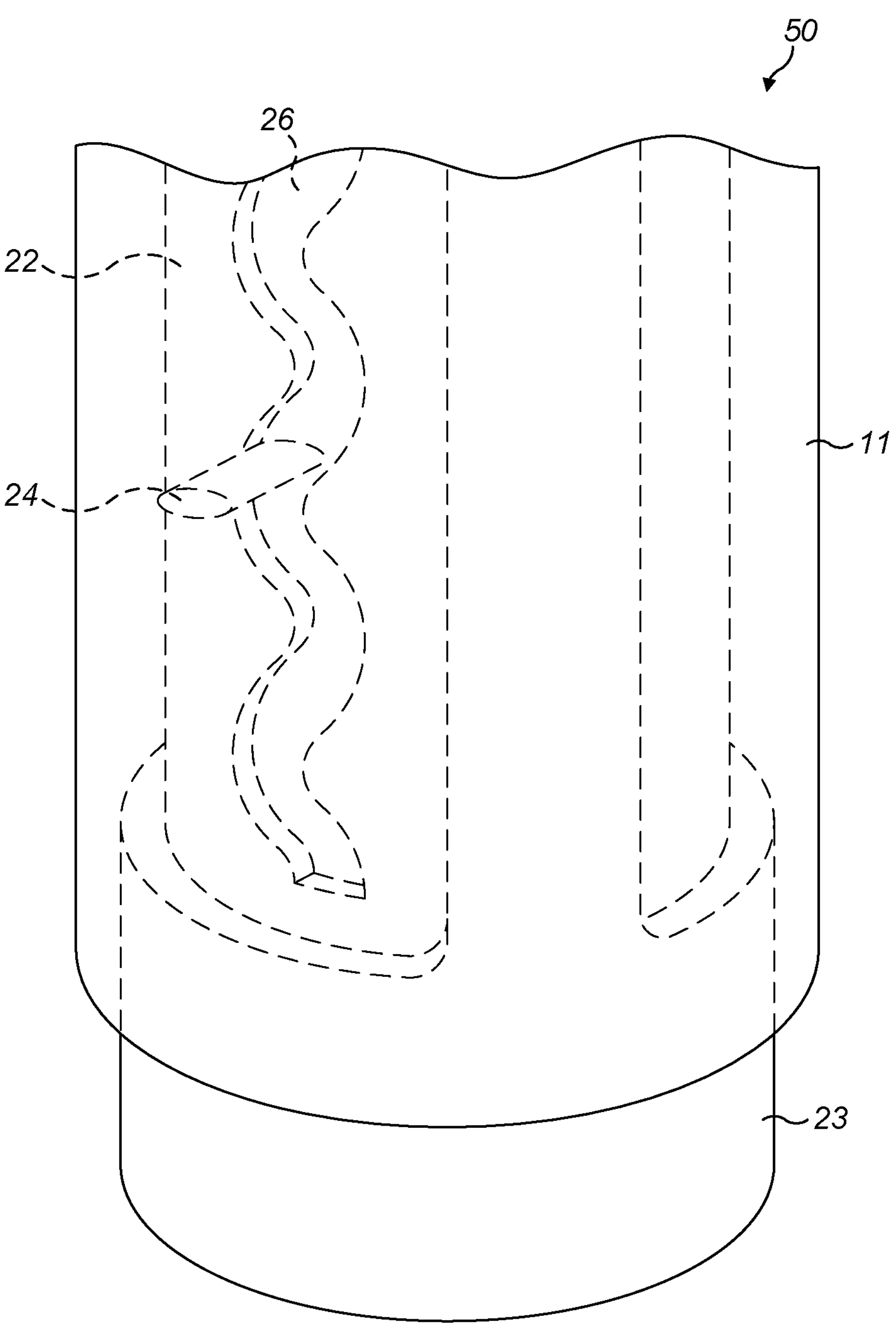
FIG. 5 shows a cutaway view of an embodiment of an injection device.

FIG. 5 shows a cutaway view of an embodiment of an injection device 50. In some embodiments, the one or more engagement features on the housing 11 are arranged to engage with one or more recessed tracks 26 on the surface of the inner sleeve 22 of the needle housing. During depression of the housing 11 in the distal direction, the one or more engagement portions 24 ride within the tracks 26 on the inner sleeve 26, transferring force/energy from the housing 11 to the inner sleeve 22 to cause the distraction portion to vibrate and/or rotate.

Properties of the one or more tracks 26 may be tailored to produce different effects on the motion of the inner sleeve 22/distraction portion 21. In some embodiments, the one or more tracks 26 may extend around the inner sleeve 22 in a spiral. The engaging features 24 will then cause the inner sleeve 22 to rotate as the housing 11 is depressed. In some embodiments, the one or more tracks 26 may be in the form of a zig-zag on the surface of the inner sleeve 22. The engaging features 24 will then cause the inner sleeve 22 to oscillate/vibrate as the housing 11 is depressed. The one or more tracks 26 may be a combination of a spiral and zig-zag in order to provide both rotational and vibrational motion to the inner sleeve 22/distraction portion 21 as the housing 11 is depressed.

In some embodiments, multiple engaging portions 24 may be received in the track 26. Multiple tracks may 26 may be present on the surface of the inner sleeve 22, each coupled to one or more different engaging portions 24. These features can assist in stabilising the injection device 50 during use.

In some embodiments, the engaging portions comprise a ratchet arrangement configured to resist movement of the needle sleeve between the extended and retracted positions and to not resist movement of the needle sleeve between the retracted and extended positions. The engagement portions 24 may be hinged so that fold back when the housing 11 is displaced relative to the needle housing 19 in the proximal direction (i.e., when the needle housing 19 is moving between the retracted and extended positions) but remain extended and engaged with the needle sleeve 19 when the housing 11 is displaced relative to the needle housing 19 in the distal direction (i.e. when the needle housing 19 is moving between the extended and retracted positions). This can reduce resistance during retraction of the needle 17 from the body.

Figure 6C:
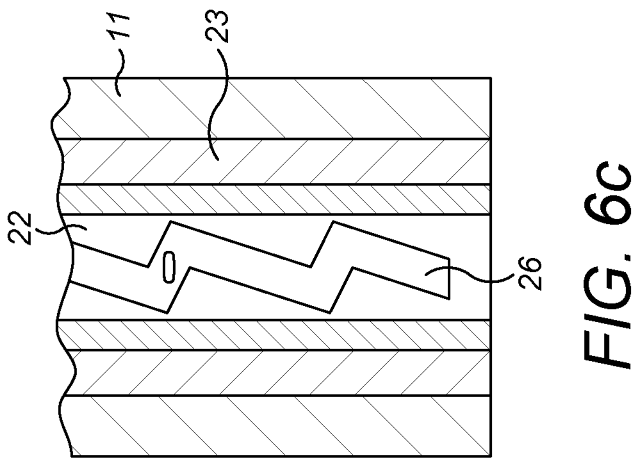
FIGS. 6*a-c* show examples of tracks for use on the inner sleeve of a needle housing.
Figure 6B:
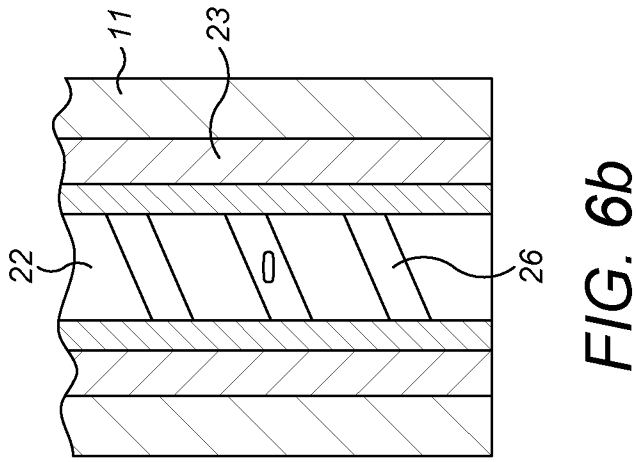
Figure 6A:
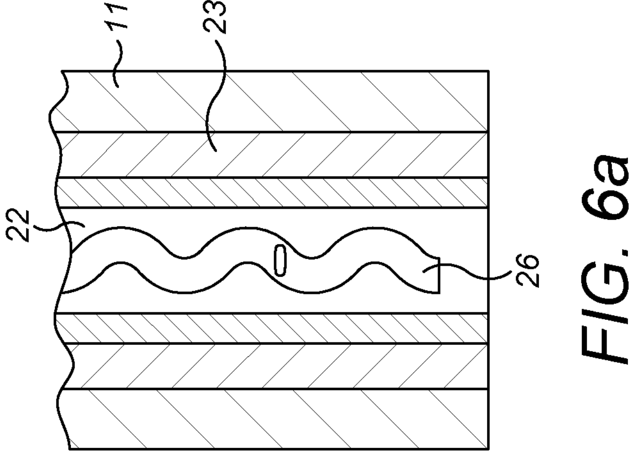

FIGS. 6*a-c* show examples of tracks 26*a-c* for use on a needle housing 19. By altering the shape of the track 26, different sensations can be achieved on the skin of the user. In the examples shown, the needle sleeve 19 comprises an inner sleeve 22 with the tracks 26*a-c* and an outer sleeve 23. However, the tracks may alternatively form part of a single needle sleeve 19.

FIG. 6*a* shows an oscillating track 26*a* on the surface of the inner sleeve 22. The oscillating track 26*a* provides a substantially smooth "wavy" track on the inner sleeve 22. When the housing 11 is depressed, engagement features 24 (not shown) of the housing 11 that are coupled to the track 26*a* cause the inner sleeve 22 to oscillate around the longitudinal axis A-A. In some embodiments, a single oscillating track 26*a* is provided. Alternatively, two or more oscillating tracks 26*a* may be provided that are offset around the longitudinal axis A-A.

FIG. 6*b* shows a spiral track 26*b* on the surface of the inner sleeve 22. The spiral track 26*b* extends around the inner sleeve 22. When the housing 11 is depressed, engagement features 24 (not shown) of the housing 11 that are coupled to the track 26*b* cause rotation of the inner sleeve 22. In some embodiments, a single spiral track 26*b* is provided. Alternatively, two or more offset spiral tracks 26*b* may be provided.

FIG. 6*c* shows a zig-zag track 26*c* on the surface of the inner sleeve 22. The zig-zag track 26*c* provides a sharp, stepped track on the inner sleeve 22. When the housing 11 is depressed, engagement features 24 (not shown) of the housing 11 that are coupled to the track 26*c* cause the inner sleeve 22 to vibrate/oscillate sharply around the longitudinal axis A-A. In some embodiments, a single zig-zagged track 26*c* is provided. Alternatively, two or more zig-zagged tracks 26*c* may be provided that are offset around the longitudinal axis A-A.

In some embodiments, the vibrating and/or rotating portion may comprise one or more piezoelectric devices. Motion of the injection device between the first configuration and the second configuration may cause the piezoelectric devices to generate electricity that causes vibration and/or rotation of the vibrating and/or rotating portion. Alternatively or additionally the generated electricity may be used to apply a mild shock to the skin of the patient to distract them from the sensation of the needle entering the skin.

The embodiments of injector devices described herein are configured to receive either a cartridge of medicament or a syringe pre-filled with a medicament. Herein, the term "medicament container" is intended to encompass both a cartridge of medicament and a pre-filled syringe.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(w-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms “Complementarity-determining region” or “CDR” refer to short polypeptide sequences within the variable region of both heavy and light chain polypeptides that are primarily responsible for mediating specific antigen recognition. The term “framework region” refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injector device comprising:
- an elongate housing having a proximal end and a distal end, the elongate housing being configured to receive a container of medicament;
- a needle housing for holding a needle in a position at the distal end of the elongate housing; and
- a needle sleeve mounted within the elongate housing,
- wherein the needle sleeve and the needle housing are moveable relative to one another by a user action between a first configuration in which the needle sleeve would enclose a needle held in the needle housing, and a second configuration in which the needle held in the needle housing would extend from the needle sleeve in a distal direction,
- wherein the needle sleeve comprises a portion configured to vibrate and/or rotate using energy from the user action during motion between the first configuration and the second configuration,
- wherein the needle sleeve comprises an outer sleeve and an inner sleeve, the inner sleeve comprises the portion configured to vibrate and/or rotate, and the outer sleeve extends beyond the inner sleeve in the distal direction.

2. The injection device of claim 1, wherein:
- in the first configuration the needle sleeve is in an extended position in which the needle sleeve at least partially extends from the distal end of the elongate housing; and
- in the second configuration the needle sleeve is in a retracted position in which the needle sleeve is received further within the elongate housing than in the extended position.

3. The injector device of claim 2, wherein the needle housing is substantially fixed relative to the elongate housing such that the needle is shrouded when the needle sleeve is in the extended position and the needle is exposed when the needle sleeve is in the retracted position.

4. The injection device of claim 2, wherein:
- the inner sleeve comprises one or more recessed tracks; and
- the elongate housing comprises one or more engaging portions arranged to couple with the one or more tracks to cause vibration and/or rotation of the inner sleeve during motion of the needle sleeve between the extended position and the retracted position.

5. The injection device of claim 4, wherein the one or more recessed tracks extend in a spiral around the inner sleeve and wherein the inner sleeve is free to rotate relative to the elongate housing.

6. The injection device of claim 5, wherein the one or more recessed tracks are in a form of a zig-zag on a surface of the inner sleeve, thereby causing the inner sleeve to vibrate during motion between the first configuration and the second configuration.

7. The injection device of claim 4, wherein the one or more engaging portions comprise a ratchet arrangement configured to resist movement between the first and second configurations and to not resist movement between the second and first configurations.

8. The injection device of claim 1, wherein the portion of the needle sleeve configured to vibrate and/or rotate comprises one or more brushes extending in the distal direction.

9. The injection device of claim 1, wherein the portion of the needle sleeve configured to vibrate and/or rotate comprises one or more protrusions and/or ridges extending in the distal direction.

10. The injection device of claim 1, wherein the portion of the needle sleeve configured to vibrate and/or rotate comprises one or more piezoelectric devices.

11. The injection device of claim 1, wherein the injection device further comprises:

a piston rod moveable longitudinally within the elongate housing; and a piston spring configured to bias the piston rod towards a distal end of the housing to engage the container of medicament when received within the elongate housing, wherein the needle sleeve is configured to suppress vibration and/or rotation of the portion during longitudinal motion of the piston rod in the distal direction.

12. The injection device of claim 1, wherein the injection device further comprises:

a piston rod moveable longitudinally within the elongate housing; and a piston spring configured to bias the piston rod towards a distal end of the housing to engage a container of medicament when received within the elongate housing, wherein the portion of the needle sleeve configured to vibrate and/or rotate is further configured to vibrate and/or rotate during longitudinal motion of the piston rod in the distal direction.

13. The injection device of claim 1, wherein the needle sleeve is fixed relative to the elongate housing, and wherein:

in the first configuration the needle housing is in a retracted position in which the needle held in the needle housing is shrouded by the needle sleeve; and in the second configuration the needle housing is in an extended position in which the needle in the needle housing extends beyond the needle sleeve in the distal direction.

14. The injection device of claim 1, further comprising the needle for expelling medicament from the injection device, the needle held in a position at the distal end of the elongate housing that is substantially fixed relative to the elongate housing such that the needle is shrouded when the needle sleeve is in the extended position and the needle is exposed when the needle sleeve is in a retracted position.

15. A method of using the injection device of claim 1, the method comprising:

preparing the injection device in the first configuration; and applying a user action to change the configuration of the injector device from the first configuration to the second configuration.

16. A method for causing vibration and/or rotation of a portion of a distal end of an injection device, the injection device having a distal end and a proximate end, the distal end comprising a needle sleeve and a needle, the method comprising:

moving, under a user action, the injection device between a first configuration, in which a needle sleeve encloses the needle, and a second configuration, in which the needle extends beyond the needle sleeve in the distal direction; and vibrating and/or rotating the portion of the distal end of the injection device during motion between the first configuration and the second configuration using energy from the user action, wherein the needle sleeve comprises an outer sleeve and an inner sleeve, the inner sleeve comprises the portion configured to vibrate and/or rotate, and the outer sleeve extends beyond the inner sleeve in the distal direction.

17. The method of claim 16, wherein moving the injection device between the first configuration and the second configuration comprises retracting the needle sleeve from an extended position in which the needle sleeve at least partially extends from an elongate housing of the injection device.

18. The method of claim 16, wherein moving the injection device between the first configuration and the second configuration comprises extending the needle from a retracted position in which the needle held in the needle housing is shrouded by the needle sleeve, wherein the needle sleeve is fixed relative to a housing of the injection device.

* * * * *